(12) United States Patent
Vartiainen

(10) Patent No.: US 8,837,668 B2
(45) Date of Patent: Sep. 16, 2014

(54) MOVEMENT MECHANISM FOR DENTAL X-RAY APPARATUS

(75) Inventor: Sami Vartiainen, Vantaa (FI)

(73) Assignee: PaloDEx Group Oy, Tuusula (FI)

(*) Notice: Subject to any disclaimer, the term of this patent is extended or adjusted under 35 U.S.C. 154(b) by 465 days.

(21) Appl. No.: 13/381,733

(22) PCT Filed: Jun. 23, 2010

(86) PCT No.: PCT/FI2010/050537
§ 371 (c)(1),
(2), (4) Date: Jan. 30, 2012

(87) PCT Pub. No.: WO2011/001025
PCT Pub. Date: Jan. 6, 2011

(65) Prior Publication Data
US 2012/0148014 A1    Jun. 14, 2012

(30) Foreign Application Priority Data
Jul. 1, 2009    (FI) .................................... 2009 5747

(51) Int. Cl.
*A61B 6/14*    (2006.01)
*A61B 6/00*    (2006.01)
*A61B 6/04*    (2006.01)

(52) U.S. Cl.
CPC ................. *A61B 6/4452* (2013.01); *A61B 6/14* (2013.01); *A61B 6/4429* (2013.01); *A61B 6/04* (2013.01)
USPC ........................................................ 378/39

(58) Field of Classification Search
CPC ...... A61B 6/4452; A61B 6/4429; A61B 6/14; A61B 6/032; A61B 6/501; A61B 6/0478
USPC ............................ 378/4–20, 38–40, 193–197
See application file for complete search history.

(56) References Cited

U.S. PATENT DOCUMENTS

| 4,754,137 A * | 6/1988 | Saotome et al. .............. 250/583 |
| 2004/0190678 A1 | 9/2004 | Rotondo et al. |
| 2008/0137802 A1 | 6/2008 | Suzuki et al. |
| 2009/0041191 A1 | 2/2009 | Suzuki et al. |

FOREIGN PATENT DOCUMENTS

| FI | 103177 B1 | 5/1999 |
| FI | 20085939 A | 4/2010 |
| JP | 6-078919 A | 3/1994 |
| JP | 2001-518341 A | 10/2001 |
| JP | 2007-143948 A | 6/2007 |
| JP | 2008-114056 A | 5/2008 |

(Continued)

OTHER PUBLICATIONS

International Search Report for parent application PCT/FI2010/050537, having a mailing date of Oct. 11, 2010.

(Continued)

*Primary Examiner* — Courtney Thomas
(74) *Attorney, Agent, or Firm* — Andrus Intellectual Property Law, LLP

(57) ABSTRACT

A movement mechanism joins an X-ray source and X-ray detector unit, adapted to rotate about the subject of the imaging. The movement mechanism comprises at least two parts adapted to be mutually turnable. In addition, the X-ray source and X-ray detector unit are located in different parts in the movement mechanism.

18 Claims, 4 Drawing Sheets

(56) References Cited

FOREIGN PATENT DOCUMENTS

| | | |
|---|---|---|
| JP | 2009-072508 A | 4/2009 |
| JP | 2009-136421 A | 6/2009 |
| WO | 2008/028988 A1 | 3/2008 |

OTHER PUBLICATIONS

Notification of Reason for Refusal issued in corresponding Japanese Patent Application No. 2012-518101, drafted Nov. 1, 2013

* cited by examiner

MOVEMENT MECHANISM FOR DENTAL X-RAY APPARATUS

CROSS-REFERENCE TO RELATED APPLICATIONS

This application is the U.S. national stage application of International Application No. PCT/FI2010/050537, filed Jun. 23, 2010, which International application was published on Jan. 6, 2011 as International Publication No. WO 2011/001025 A1 in the English language and which application is incorporated herein by reference. The International application claims priority of Finnish Patent Application No. 20095747, filed Jul. 1, 2009, which application is incorporated herein by reference.

The invention relates to a movement mechanism for a dental X-ray apparatus, particularly an extraoral dental X-ray apparatus, for supporting an X-ray source and/or X-ray detector connected with said apparatus and/or for moving them about a subject to be imaged.

PRIOR ART

There exist several widely used X-ray imaging methods, e.g. cone beam computed tomography (CBCT, in which a subject can be imaged using e.g. symmetrical computed tomography where the source and detector of radiation rotate 180°-360° about the subject imaged or where offset imaging can be used with e.g. 360° rotation) as well as methods used in panoramic and cephalostatic imaging, among others. Common to all these is the fact that the subject to be imaged is placed between an X-ray-emitting source of radiation and an X-ray detector.

In prior-art solutions the placement and the passage of the patient between the X-ray source and X-ray detector can be problematic because space is limited and components of equipment are hindering movement. Easy placement of the patient in the manner required by various imaging programs is, however, very important from the imaging standpoint. Incorrect placement may result in failed imaging in which case the patient may have to be irradiated more than what was planned. On the other hand, one factor in successful patient placement is that the operator of the X-ray device sees the patient properly, without any part of the machinery obstructing his/her view. Cramped spaces and the components' sensitivity and susceptibility to damage also make the placement of the patient more difficult and slow. The components, e.g. the X-ray detector, are also very expensive.

The single most expensive component in an X-ray imaging device is usually the X-ray detector the price tag of which primarily depends on the size of the detector so that the bigger the detector the more expensive it is. The size of the detector dictates the size of the image area. To get a larger image area one usually needs a larger detector. For example, X-ray detectors suitable for cone beam computed tomography (CBCT) have large areas which also means that the CBCT devices are big and expensive. Large detectors also demand a lot from the X-ray source since the primary cone beam needs to be of good quality throughout the image area of the detector.

However, offset techniques, for example, are known from the prior art (FI20085939) for producing a larger image area with a smaller detector than in conventional techniques. In offset imaging, an image is taken in one or more parts so that a larger image area can be obtained e.g. by computationally combining two smaller ones.

For example, in offset imaging disclosed in application FI20085939, comprising a plurality of imagings, the detector has to be moved laterally with respect to the axis of rotation of the X-ray apparatus between the first and second imaging movements. The lateral movement of the detector typically equals the width of the detector, approximately. Since the usable cone beam produced by the X-ray source is usually narrower than the area covered by this movement, also the X-ray beam or X-ray source must be turned when the detector is moved. The X-ray beam can be directed e.g. by turning the X-ray source, and the cone beam can be cropped or parts of it can be selected using a collimator between the X-ray source and detector.

Imaging devices according to the prior art also have some other problems, e.g. when used for taking cephalostatic or panoramic images (U.S. 2004/0190678 A1, WO 2008/028988 A1, FI 103177 B). In known cephalostatic imaging, an X-ray detector intended for other imaging functions is often removed from the support arm and an X-ray detector for cephalostatic imaging is attached to the device by means of a separate support arm, for example. As for an X-ray detector for panoramic imaging, it should be placed closer to the X-ray source than e.g. a CT imaging detector (using the correct source image distance, SID). The removal and/or shifting of the X-ray detector always involves the risk that the detector is dropped and gets damaged.

FIG. 1 shows a prior-art imaging device in which the X-ray source 12 and detector 11 are attached to a movement mechanism, so-called rotator, where the movement mechanism is a monolithic fixed boom 10 pivoted onto the imaging device and adapted to rotate so that the X-ray source and detector move about the subject 13 imaged. The problem here is the above-mentioned difficulty in patient movement and/or placement.

FIG. 2 shows a second prior-art imaging device where the movement mechanism comprises a plurality of parts 20a, 20b. The problem with this solution is that the X-ray source 22 and detector 21 cannot freely rotate about the subject 23, e.g. making a full circle, since the components of the movement mechanism hinder one another and, on the other hand, the construction is rather complicated.

SUMMARY OF INVENTION

An object of the invention is to eliminate certain problems and disadvantages associated with the prior art. According to one embodiment, for example, the invention aims to make it easier to place the patient for the imaging process as well as to make it easier and quicker to arrange the dental X-ray apparatus between different imaging positions.

Objects of the invention are achieved with a movement mechanism for a dental X-ray apparatus according to claim 1 and extraoral dental X-ray apparatus according to claim 18.

The movement mechanism for a dental X-ray apparatus according to the invention is characterized in that which is specified in claim 1 directed to the movement mechanism, and the extraoral dental X-ray apparatus according to the invention is characterized in that which is specified in claim 18 directed to the extraoral dental X-ray apparatus.

An embodiment of the invention concerns a movement mechanism for a dental X-ray apparatus joining an X-ray source and X-ray detector unit and makes it possible to move them relative to each other. The movement mechanism is furthermore adapted to be rotatable about the subject imaged. An exemplifying movement mechanism according to the invention comprises at least two parts adapted to be turnable relative to each other so that the X-ray source and X-ray detector unit are placed in different parts in the movement mechanism. Advantageously the parts are arranged such that they make it possible for the X-ray source and X-ray detector unit to rotate 360° about the subject imaged.

According to one example, a part of the movement mechanism connected with the X-ray source and/or X-ray detector unit is adapted such that it can be turned aside e.g. for the duration of patient placement so that both the X-ray source and the X-ray detector unit are on the same side of the axis of rotation of the movement mechanism so that the X-ray source and/or detector do not obstruct the placement. In one embodiment, also the axis of rotation is adapted to be movable sideways with respect to the beam emitted by the X-ray source.

An arrangement like the one described above makes it possible to turn the parts of the movement mechanism into a position such that there are no parts between the patient and the X-ray apparatus which would obstruct visibility or hamper the patient placement. The part comprising the detector and the part comprising the X-ray source can be turned onto the opposite side of the user so as to be completely invisible from the patient placement standpoint. It should be noted that mutual turnability of the parts can be achieved by joining the parts together, for instance. It should also be noted that the joining points can be completely freely chosen. The joining itself can be implemented using techniques known to a person skilled in the art.

The movement mechanism according to the invention may comprise two or more parts joined together at the axis of rotation, for example. The joint may be in the middle of the movement mechanism or elsewhere. The parts may be joined together using e.g. an extra bearing or other bearings located axially with respect to the bearing used in the rotation of the movement mechanism. According to one example, the mutual turnability of the parts of the movement mechanism is adapted to occur with respect to an axis congruent with the axis of rotation.

According to one embodiment, the movement mechanism comprises a center part axially attached through a bearing to the axis used in the rotation of the movement mechanism and at least one second part connected with the center part in a turnable manner and an X-ray detector unit or X-ray source connected with the second part in a turnable manner. Thus the movement mechanism can be folded in two parts (the movement mechanism comprises e.g. a center part attached to a bearing) whereby the X-ray source and/or detector can be e.g. hinged in a turnable manner to said at least one second part. Mutual turnability of the parts can be implemented e.g. through bearings, joints and/or hinges.

When turning parts connected with the X-ray source and/or detector simultaneously, the movement mechanism can be arranged to include a bearing point at the X-ray source end and/or at the detector end. In addition there may be a mechanism, e.g. a forced control mechanism, between these and the body, which mechanism makes them move with respect to each other.

According to one embodiment, the at least two parts of the movement mechanism are adapted to turn with respect to each other when the movement mechanism is driven around its axis of rotation up to its rotation limit or up to some other point which triggers the turning of said parts. The turning of the parts with respect to each other and/or positions of the X-ray detector and X-ray source can be controlled using forced control, for instance. The forced control can be implemented using a technique known to a person skilled in the art, e.g. through levers, cables, push rods and/or cogwheels. The forced control can be controlled either manually without a motor, e.g. by turning some part of the movement mechanism, with a crank or other lever arm, or using a motor. According to one embodiment, the turning of the part connected with the X-ray source, for instance, can be implemented using a dedicated motor if a forced control mechanism were too expensive and/or complicated to implement.

In one embodiment it is possible to have a folding joint in the movement mechanism, e.g. the middle joint, with associated forced controlled turning of the X-ray source and X-ray detector without a single additional motor so that the middle joint of the movement mechanism is turned by means of the rotation motor of the movement mechanism. In this model the movement mechanism can be driven e.g. to either of its mechanical rotation limits or to some other limit, and rotation after that will not rotate the movement mechanism but will instead bend the middle joint of the movement mechanism and thereby also move the X-ray source and/or X-ray detector. What is essential in this model is that the mechanical rotation limit affects a different half in the jointed movement mechanism than the rotation motor.

According to one embodiment, the X-ray detector unit only comprises one X-ray detector and it is adapted to be used in various types of CT imaging, e.g. symmetrical CT imaging and/or offset imaging. In that case the positions of the X-ray source and X-ray detector unit associated with parts of the movement mechanism or the collimation of X-rays are adapted to change when the parts of the movement mechanism are turned with respect to each other e.g. between the symmetrical CT imaging and offset imaging positions or between different offset imaging positions so that the center beam of the X-ray cone beam emitted by the X-ray source or some other reference beam hits the X-ray detector unit or an X-ray detector. It is advantageous that the beam hits the detector substantially perpendicularly.

According to one embodiment, the one and the same detector can be used in panoramic imaging whereby the parts of the movement mechanism are adapted to move when they are turned with respect to each other so that the detector will move closer to the X-ray source within the cone beam of the X-ray source, achieving the correct distance, or SID, between the point of focus of the X-ray source and the detector.

According to one example, a very narrow X-ray detector can be used e.g. in offset imaging in accordance with the present invention. Furthermore, the invention makes it possible to turn the detector and/or X-ray source or collimate the beam between various imaging positions so that the X-ray beam hits the detector preferably as perpendicularly as possible. However, deviations can be corrected by software, for example. The present invention facilitates taking relatively large images using a quite narrow detector which, being narrow, is also not so expensive.

According to one embodiment the X-ray detector unit comprises two separate X-ray detectors, a first one for CT imaging (e.g. symmetrical CT imaging and offset imaging), for example, and a second one for panorama imaging, for example. Also in this embodiment the positions of the X-ray source and X-ray detector unit or the collimation of X-rays are adapted to change when the at least two parts of the movement mechanism are turned with respect to each other e.g. between CT imaging and panorama imaging positions so that the X-ray beam emitted by the X-ray source hits the X-ray detector preferably as perpendicularly as possible and the correct SID is obtained, among other things. According to one embodiment, also the positions of individual detectors can be changed when turning the at least two parts of the movement mechanism with respect to each other between different imaging positions.

One embodiment of the invention relates to a movement mechanism where the part of the movement mechanism meant for the primary X-ray detector unit used in CT and panoramic imaging, for example, is adapted to be turned aside during cephalostatic imaging, for instance, so that the X-ray beam emitted by the X-ray source will propagate substantially unobstructed onto the X-ray detector used for cephalostatic imaging. It should be noted that the X-ray detector used for cephalostatic imaging is placed at a different distance, typically much farther, from the X-ray source than in CT and/or panoramic imaging. In cephalostatic imaging the X-ray detector is placed e.g. at the end of a special arm, or it can be attached to a wall or other support element or to some other component in connection with said dental X-ray apparatus. The support arm or support element may be physically completely detached from the X-ray apparatus and its movement mechanism. It should be noted that the detector used in cephalostatic imaging can be the same as that used in CT or panoramic imaging, for example, so that the detector can be disconnected from the part of the movement mechanism, the part of the movement mechanism can be turned aside, and the detector can be attached to a support means like those mentioned above.

Furthermore, one embodiment of the invention relates to a movement mechanism where the part of the movement mechanism which is meant for the primary X-ray source used in CT and panoramic imaging, for example, is adapted to be turned aside during cephalostatic imaging. In that case the X-ray source used for cephalostatic imaging can be placed at an end of a special support arm or other support element or is adapted to be placed on some other part connected with the dental X-ray apparatus, for instance. The support means for the X-ray source can be physically completely detached from the X-ray apparatus and its movement mechanism.

The invention offers significant advantages. For example, the positions of the X-ray source, collimator and/or X-ray detector with respect to the axis of rotation used in the imaging movement which are made possible by the movement mechanism according to the invention, facilitate e.g. both symmetrical CT imaging and offset-type CT imaging and also panoramic imaging as well as cephalostatic imaging in one and the same apparatus. Furthermore, one and the same mechanism brings a considerable advantage at the patient placement stage since the X-ray source and detector can be turned aside so as not to hamper the patient placement. In addition, said movement mechanism makes it possible, in one embodiment of the invention, to bring the panoramic detector to a correct distance for panoramic imaging because, when turned extensively aside, the X-ray detector unit or detector moves closer to the X-ray source. Furthermore, in one embodiment of the invention, the movement mechanism makes it possible to change the offset also during imaging. At its most versatile, the movement mechanism according to the invention which comprises at least two parts brings about all the above-mentioned advantages in one and the same apparatus.

In one simple embodiment, the movement mechanism would comprise a structure with a central joint so that the movement mechanism would essentially constitute two mutually rotating halves which can be rotated to the same side of the axis of rotation for the duration of patient placement. In that case, turnability of the detector unit and X-ray source, for instance, could be left unimplemented.

In addition, the invention has the advantage that the mechanism needed to move the X-ray source and detector becomes simpler by arranging the movement mechanism, at the axis of rotation, for example, into two parts by means of a joint. Thus the mutual movement of the X-ray source and detector can be accomplished, at its simplest, by bending the movement mechanism at its central joint. Depending on the imaging geometry, slight turning of the detector part and/or X-ray source may also be needed but these movements can be driven, using forced control, for example, by the same movement motor that is used for actuating the bending of the central joint of the movement mechanism.

One significant advantage of the invention is that the foldable movement mechanism facilitates, in addition to symmetrical CT imaging and offset imaging, also panoramic imaging e.g. by placing the panoramic imaging detector next to the CT imaging detector in the detector unit and bending the parts of the movement mechanism with such amount that the panoramic imaging detector will move to the right spot in the beam. As this bending of the movement mechanism brings the panoramic imaging detector closer to the X-ray source, the correct SID for panoramic imaging, which is usually shorter than that for CT imaging, will be achieved.

Furthermore, the movement mechanism according to the invention, which comprises at least two parts, makes it possible to upgrade the system in a versatile manner because both the X-ray detector and/or X-ray source or associated components can be replaced completely independently. Additionally it should be noted that the idea of the invention can be utilized in all known dental imaging devices, e.g. devices intended for patients in standing or sitting position. Furthermore, in panoramic imaging, for example, it is possible to use the CT imaging detector by just moving the detector closer to the X-ray source and using a narrow vertical strip of the detector.

Advantageous embodiments of the invention are presented in the dependent claims.

DESCRIPTION OF DRAWINGS

Advantageous embodiments of the invention will be described below a little more closely, referring to the accompanying drawings in which.

DETAILED DESCRIPTION OF DRAWINGS

Figure 1:
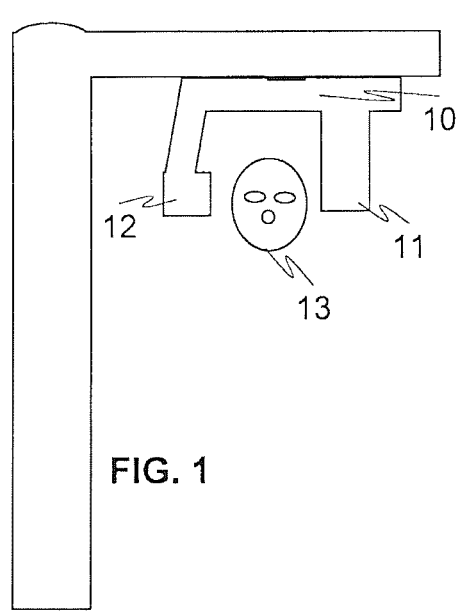
FIG. 1 shows an imaging apparatus according to the prior art.
Figure 2:
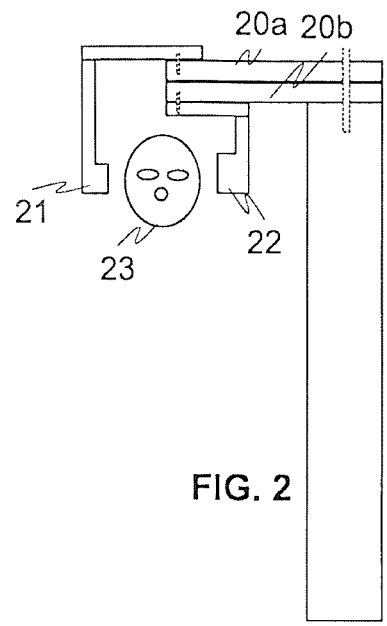
FIG. 2 shows another imaging apparatus according to the prior art.

FIGS. 1 and 2 show prior-art solutions and were described earlier in this document in the section dealing with the prior art.

Figure 3A:
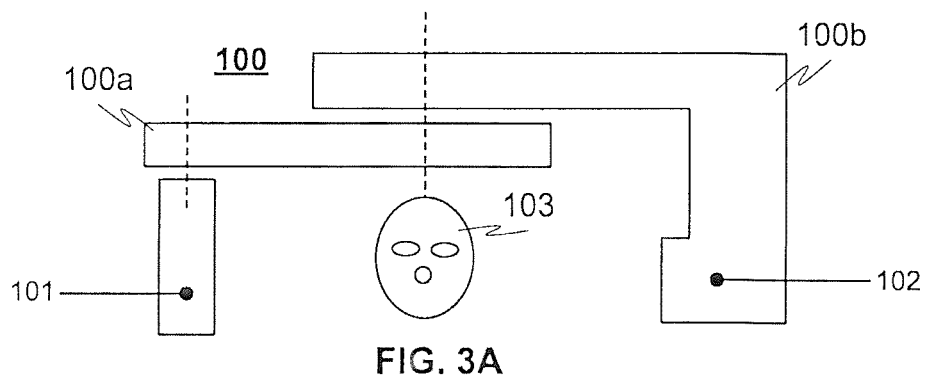
FIG. 3A shows a side view of an exemplifying movement mechanism according to the invention.

FIG. 3A shows a side view of an exemplifying movement mechanism 100 of an extraoral dental X-ray apparatus according to the invention. The movement mechanism 100 comprises at least two parts 100a, 100b adapted so as to turn with respect to each other, with an X-ray detector unit 101 fitted in the first part 100a and an X-ray source 102 in the second part 100b. In addition, the movement mechanism is adapted so as to rotate about a subject 103 imaged, either a full circle or at least a partial circle or an ellipse when the center of rotation moves with respect to the object. The movement mechanism shown in the Figure comprises two parts joined together at the axis of rotation, but it should be noted that the parts could be interconnected at some other point as well, e.g. at the area between the axis of rotation and the X-ray source or the area between the axis of rotation and the X-ray detector unit or, in one embodiment, both, whereby the movement mechanism would comprise at least three parts (not shown).

Figure 3B:
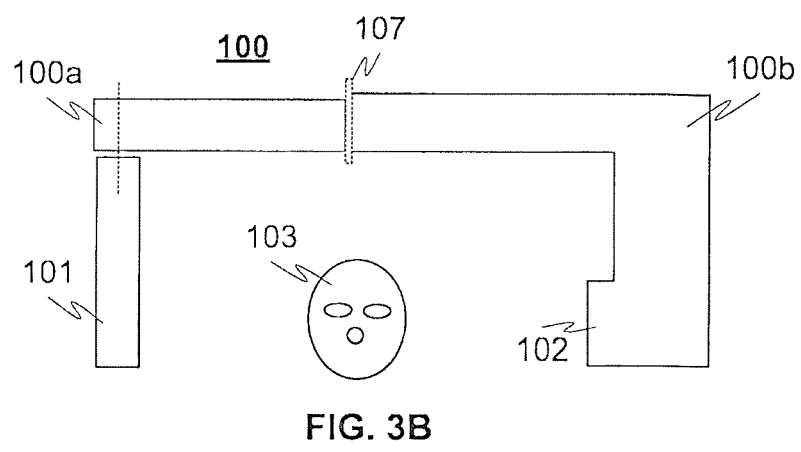
FIG. 3B shows a side view of another exemplifying movement mechanism according to the invention.

FIG. 3B shows a side view of another exemplifying movement mechanism 100 of an extraoral dental X-ray apparatus according to the invention where the parts 100a, 100b of the movement mechanism are placed, unlike in FIG. 3A, in parallel, whereby the parts are advantageously joined 107 by their ends. Also the movement mechanism shown in FIG. 3B may comprise more parts than the two parts depicted in the Figure.

Figure 4:
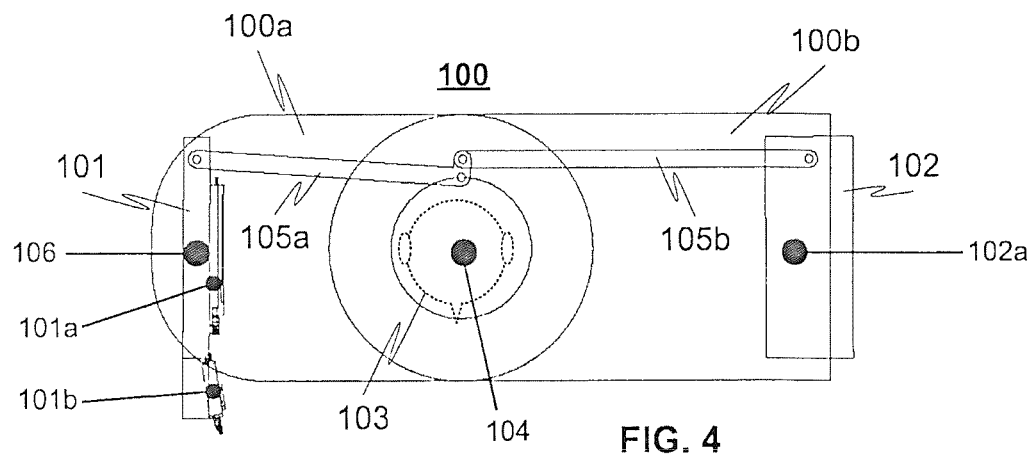
FIG. 4 shows a top view of an exemplifying movement mechanism according to the invention.

FIG. 4 shows a top view of an exemplifying movement mechanism 100 according to the invention where the first part 100a of the movement mechanism comprises an X-ray detector unit 101. The exemplifying X-ray detector unit 101 shown in FIG. 4 comprises an X-ray detector 101a for CT imaging and another X-ray detector 101b for panoramic imaging. In addition, the second part 100b of the movement mechanism comprises an X-ray source 102.

Point 104 in FIG. 4 shows a possible center of rotation and point of joining of parts 100a and 100b of the movement mechanism. It should be noted, however, that the center of rotation and/or point of joining can be arranged to be located in some other arbitrary point of the movement mechanism and the invention is by no means limited to the points shown in the drawings.

Furthermore, FIG. 4 shows an example of a forced control mechanism 105a, 105b adapted to control the positions of the X-ray unit 101 or detectors 101a, 101b, collimator (not shown), and/or X-ray source 102 when at least one part 100a, 100b of the movement mechanism is turned. The exemplifying forced control mechanism depicted in FIG. 4 is implemented using push rods 105a, 105b but the forced control can also be implemented with other techniques known to a person skilled in the art. It should also be noted that forced control is not necessarily needed in the movement mechanism according to the present invention, but the turning of the parts can be implemented in accordance with the invention without any forced control at all whereby the detector unit or associated detectors or other components in the apparatus can be controlled, moved and/or turned manually or by means of a motor, for instance.

Point 106 represents an advantageous point of joining for the detector unit so that the unit is arranged to turn about said point either through forced control or otherwise.

Figure 5:
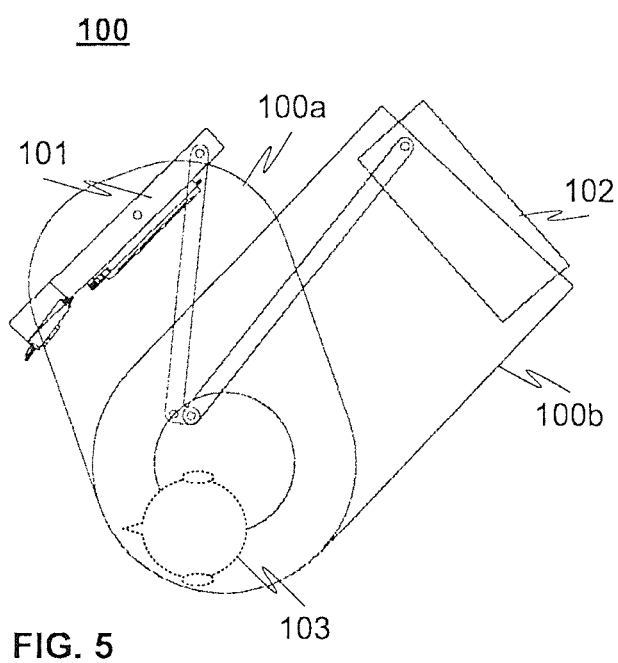
FIG. 5 shows a top view of an exemplifying movement mechanism according to the invention folded in the patient placement position.

FIG. 5 shows a top view of an exemplifying movement mechanism 100 according to the invention folded in the placement position of the patient 103. In the Figure, a part (100a and/or 100b) of a movement mechanism in the X-ray source 102 and/or X-ray detector unit 101 is turned aside e.g. for the duration of patient placement so that both the X-ray source and the X-ray detector unit are on the same side of the axis of rotation of the movement mechanism. Thus the patient 103 can be placed e.g. from that side of the axis of rotation of the movement mechanism which is opposite to the side where the X-ray source and X-ray detector unit are located so that the operator of the X-ray apparatus sees the patient properly, without any part of the apparatus obstructing his/her view.

From the point of view of the idea of the invention and patient placement it is irrelevant whether the turning part 100a, 100b in the movement mechanism is a part connected with the X-ray source 102 or X-ray detector unit 101 or both.

Figure 6:
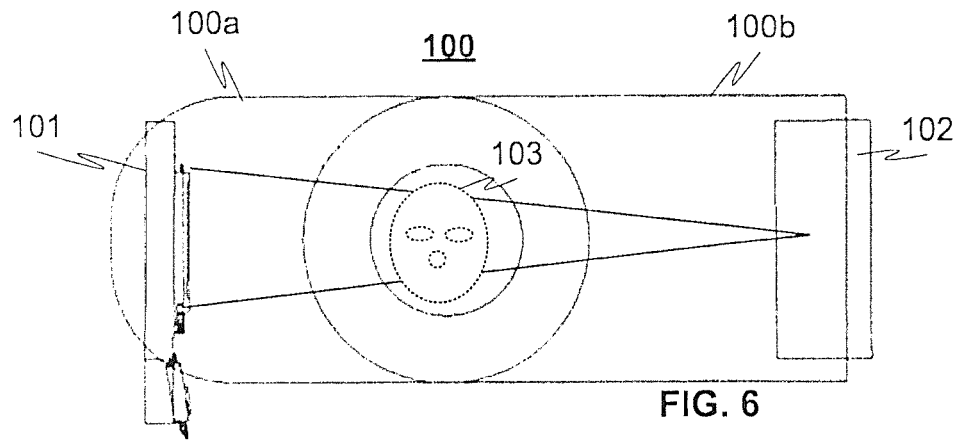
FIG. 6 shows a top view of an exemplifying movement mechanism according to the invention arranged in the CT imaging position.

FIG. 6 shows a top view of an exemplifying movement mechanism 100 according to the invention arranged in the symmetrical CT imaging position, where an X-ray source 102 is used for irradiating the subject 103 of the imaging and where the imaging is accomplished by rotating the X-ray source 102 and detector 101 about the subject 103 of the imaging.

Figure 7A:
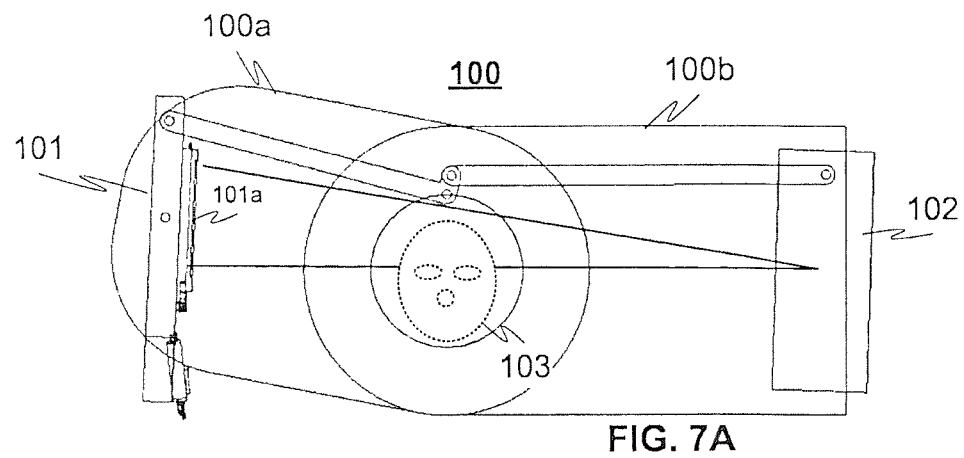
FIG. 7A shows a top view of an exemplifying movement mechanism according to the invention arranged in a first offset imaging position.
Figure 7B:
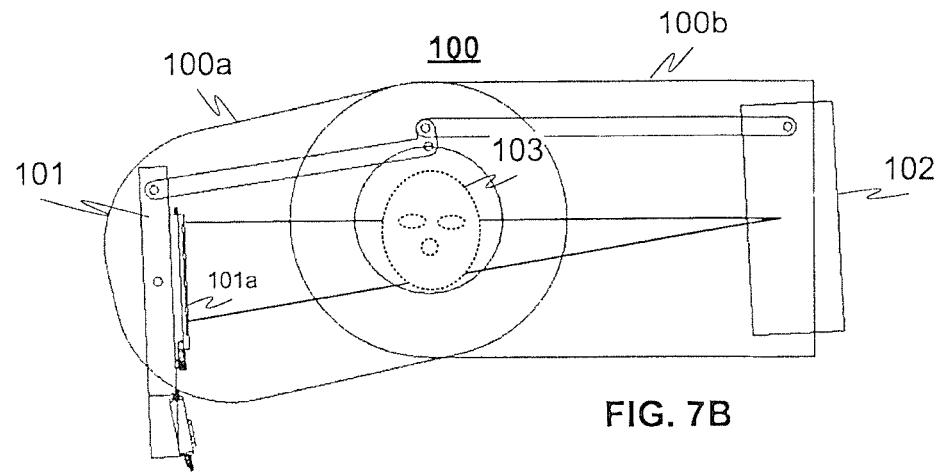
FIG. 7B shows a top view of an exemplifying movement mechanism according to the invention arranged in a second offset imaging position.

FIG. 7A shows a top view of an exemplifying movement mechanism according to the invention arranged in a first offset imaging position, and FIG. 7B shows a top view of an exemplifying movement mechanism according to the invention arranged in a second offset imaging position. In offset imaging, the center of the image area of the detector is offset from the line between the X-ray source and the center of rotation. The center line between the X-ray source and detector can be moved aside from the center of rotation located on the axis of rotation during imaging or imaging stages, for example.

In one embodiment of the invention, the positions of the X-ray source 102 and X-ray detector unit 101 or X-ray detector or also the beam-directing collimator (not shown) are adapted to change when the parts 100a, 100b of the movement mechanism, which are associated with the X-ray source and/or unit/detector, are turned with respect to each other e.g. between the symmetrical and offset imaging positions, as can be seen e.g. from the differences between the positions of the X-ray source and detector depicted in FIGS. 6 and 7A. When the movement mechanism 100 or at least one of its parts 100a, 100b is turned from the CT imaging position (FIG. 6) to a first offset imaging position (FIG. 7A), part 100a in connection with the detector unit 101 is adapted so as to become offset from the line through the X-ray source 102 and center of rotation, whereby also the center of the image area of the detector 101a will be offset from the line through the X-ray source and center of rotation. Also the position of the X-ray source 102 and/or beam-directing collimator can be changed, e.g. turned so that the X-ray beam emitted by the X-ray source will hit said X-ray detector 101a.

When the movement mechanism 100 or at least one of its parts 100a, 100b is turned from the first offset imaging position (FIG. 7A) to a second offset imaging position (FIG. 7B), part 100a in connection with the detector is adapted so as to turn to the other side of the line through the X-ray source 102 and center of rotation than in the first offset imaging position. Also in this case the position of the X-ray source 102 can be changed, e.g. turned so that the X-ray beam emitted by the X-ray source will hit said X-ray detector 101a. Furthermore, the position of the collimator can be changed so that the beam can be cropped or parts of it can be selected.

It should be noted that in offset imaging it is possible to take images with different offset settings on the same side of said center line, whereby the distance of the detector from the X-ray source will not necessarily be a constant. The change in the magnification of the image, caused by the changing distance, can be compensated for by software or correction hardware attached to the apparatus, for example.

Mutual movements of the parts, X-ray source, collimator and/or detector, as the parts are turned, can be adapted to occur by forced control, for instance, in accordance with the above examples, or they can occur without forced control, e.g. manually or motor-driven.

Figure 8:
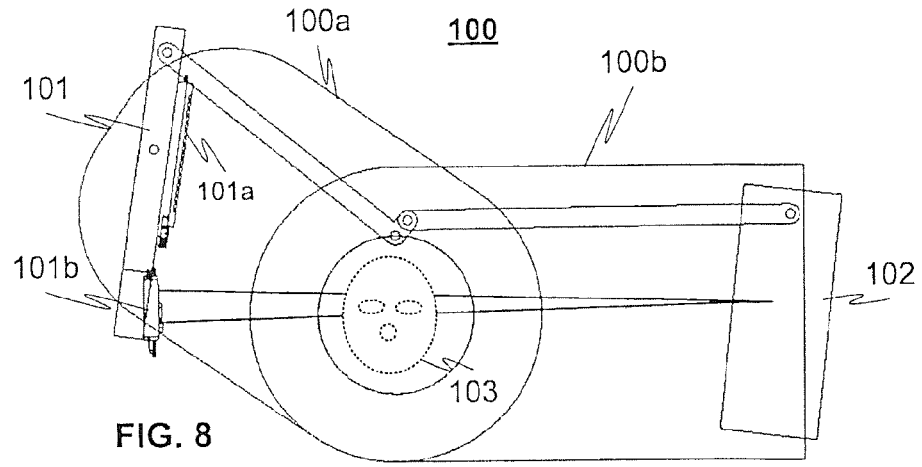
FIG. 8 shows a top view of an exemplifying movement mechanism according to the invention arranged in the panoramic imaging position.

FIG. 8 shows a top view of an exemplifying movement mechanism 100 according to the invention arranged in the panoramic imaging position. When the movement mechanism 100 or at least one of its parts 100a, 100b is turned into the panoramic imaging position, the X-ray detector unit 101 is adapted to move closer to the X-ray source 102 along the beam emitted by the X-ray source so that a shorter SID typical of panoramic imaging is achieved. Also the position of the detector 101b used in panoramic imaging, the position of the beam-directing collimator and/or that of the X-ray source 102 can be changed, e.g. turned so that the X-ray beam emitted by the X-ray source 102 will hit said X-ray detector 101b or the beam can be cropped or its parts can be selected as desired.

Figure 9A:
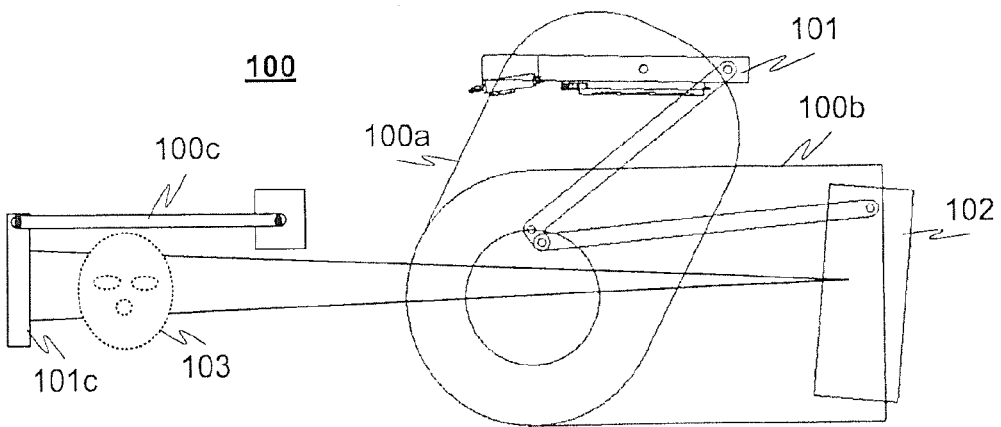
FIG. 9A shows a top view of an exemplifying movement mechanism according to the invention arranged in the cephalostatic imaging position.

FIG. 9A shows a top view of an exemplifying movement mechanism 100 according to the invention arranged in the cephalostatic imaging position. A part 100a connected with the movement mechanism meant for the main X-ray detector unit 101 used in CT and panoramic imaging, for example, is adapted to be turned aside during cephalostatic imaging so that the X-ray beam emitted by the X-ray source 102 will propagate substantially unobstructed onto the X-ray detector 101c used in cephalostatic imaging. It should be noted that the X-ray detector 101c used in cephalostatic imaging is placed at a different distance, typically much farther, from the X-ray source 102 than in CT and/or panoramic imaging. In cephalostatic imaging, the X-ray detector is placed at an end of a special support arm 100c, for example. The subject is represented by reference number 103.

It should also be noted that the detector used in cephalostatic imaging can be the same as that used in CT or panoramic imaging, for example, so that the detector can be disconnected from the part 100a of the movement mechanism, said part 100a of the movement mechanism can be turned aside, and the detector can be attached to a support means, for instance.

Figure 9B:
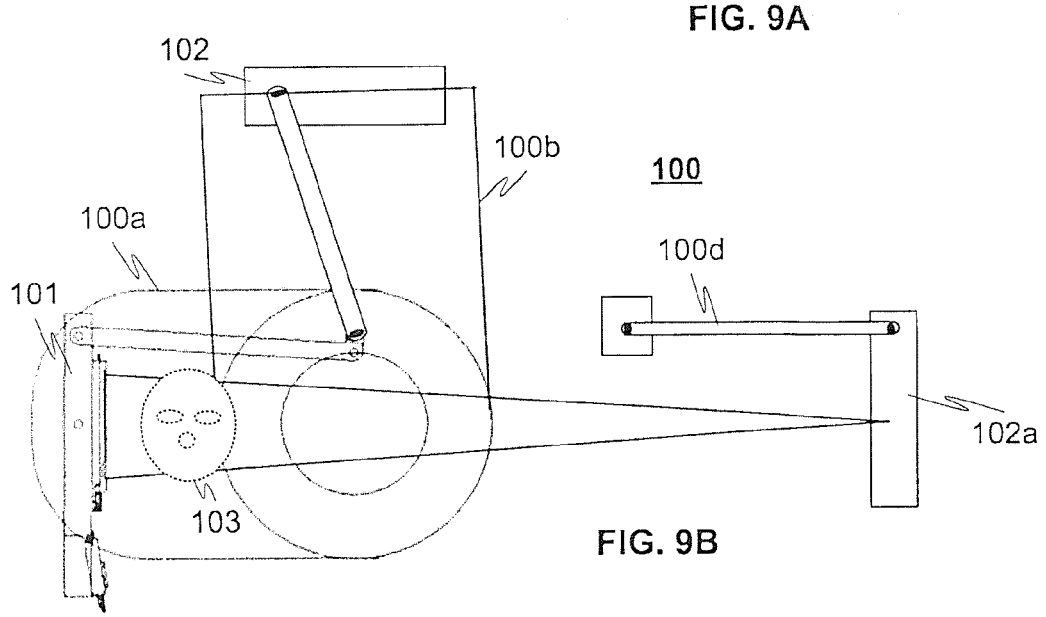
FIG. 9B shows a top view of another exemplifying movement mechanism according to the invention arranged in the cephalostatic imaging position.

FIG. 9B shows a top view of another exemplifying movement mechanism according to the invention arranged in the cephalostatic imaging position. A part 100b connected with the movement mechanism meant for the main X-ray source 102 used in CT and panoramic imaging, for example, is adapted to be turned aside during cephalostatic imaging. The X-ray source 102a used for cephalostatic imaging can be placed at an end of a special support arm or other support element or is adapted to be placed on some other part connected with the dental X-ray apparatus, for instance. Said other part may be a support means 100d physically detached from the X-ray apparatus and/or movement mechanism. The subject is represented by reference number 103.

Only a few embodiments of the solution according to the invention were described above. The principle according to the invention, as regards e.g. implementation details and field of application, may naturally be modified within the scope of the invention defined by the claims. Especially it should be noted that the parts of the movement mechanism may also be hinged or otherwise adapted to bend or fold at an arbitrary point other than the center of rotation, either on the side of the X-ray source or X-ray detector. The movement mechanism may also be adapted to fold in two parts, whereby the movement mechanism comprises a middle part attached to a bearing, and ends on the sides of the X-ray source and X-ray detector which may both be hinged or otherwise adapted to be turnable. Additionally it should be noted that the center of rotation may be mechanical or virtual and that it may move during the imaging session. A virtual center of rotation is produced e.g. by moving a mechanical center of rotation along a circular path, whereby the virtual center of rotation will be at the center of said circular path. Non-circular scanning can be achieved e.g. by moving the source and detector in a non-circular ellipse-shaped path, for example.

In addition it should be noted that during imaging the parts 100a, 100b of the movement mechanism may be in a straight line with respect to each other, like in the case depicted by FIG. 6, or they may be at an angle with respect to each other, like in the cases depicted by FIGS. 7A, 7B, and 8, for example. Furthermore, it should be noted that the movement mechanism may be arranged to rotate about its center of rotation even if the parts 100a, 100b were at an angle with respect to each other.

Still it should be noted that the detector can be moved, turned or shifted also laterally. In one embodiment, the detector can be moved sideways also in conjunction with cephalostatic imaging. In cephalostatic imaging, the detector may be e.g. a detector used in panoramic imaging, which is rather narrow, in which case the detector may be adapted to move sideways during imaging.

What is claimed is:

1. A movement mechanism for an extraoral dental X-ray apparatus, which movement mechanism joins an X-ray source and an X-ray detector unit and is adapted to rotate about the subject of the imaging and comprises at least two parts turnable with respect to each other, said X-ray source and X-ray detector unit being located in different parts of the movement mechanism, wherein in the movement mechanism the positions of the X-ray source and X-ray detector unit or X-ray detector are adapted to change when said at least two parts are turned with respect to each other between a symmetrical CT imaging position and at least one offset imaging position or between different offset imaging positions so that the X-ray beam emitted by the X-ray source hits said X-ray detector unit or X-ray detector, or said X-ray detector unit is adapted to move closer to the X-ray source along the beam of the X-ray source when a part of the movement mechanism connected with the X-ray detector unit is turned into a panoramic imaging position.

2. A movement mechanism according to claim 1, wherein the X-ray source and X-ray detector unit are placed in different parts of the movement mechanism so that the X-ray source and X-ray detector unit can rotate substantially freely about the subject of the imaging.

3. A movement mechanism according to claim 1, wherein the X-ray detector unit is adapted to be used in both CT imaging and panoramic imaging.

4. A movement mechanism according to claim 1, wherein the X-ray detector unit comprises an X-ray detector for CT imaging and an X-ray detector for panoramic imaging.

5. A movement mechanism according to claim 1, wherein a part of the movement mechanism connected with the X-ray source and/or X-ray detector unit is adapted to be turned aside e.g. for the duration of patient placement so that both the X-ray source and the X-ray detector unit are located on the same side of the axis of rotation of the movement mechanism.

6. A movement mechanism according to claim 1, wherein the axis of rotation is adapted to be movable sideways with respect to the beam emitted by the X-ray source.

7. A movement mechanism according to claim 1, wherein the movement mechanism comprises two parts mutually joined at the axis of rotation.

8. A movement mechanism according to claim 7, wherein at least two parts of the movement mechanism are mutually joined using bearings located axially with respect to the bearing used for the rotation of the movement mechanism.

9. A movement mechanism according to claim 7, wherein the mutual turning of the parts of the movement mechanism is adapted to occur with respect to an axis congruent with the axis of rotation.

10. A movement mechanism according to claim 1, wherein the movement mechanism comprises a center part axially attached through a bearing to the axis used in the rotation of the movement mechanism and at least one second part connected with the center part in a turnable manner, and an X-ray detector unit or X-ray source connected with the second part in a turnable manner.

11. A movement mechanism according to claim 1, wherein the at least two parts of the movement mechanism are adapted to turn with respect to each other when the movement mechanism is driven around its axis of rotation up to its rotation limit or up to some other point which triggers the turning of said parts.

12. A movement mechanism according to claim 1, wherein said turnings of the parts with respect to each other and/or the positions of the X-ray detector and X-ray source are controlled using forced control.

13. A movement mechanism according to claim 12, wherein said forced control is accomplished by means of at least one lever, cable, push rod and/or cogwheel.

14. A movement mechanism according to claim 13, wherein said forced control is driven by a motor.

15. A movement mechanism according to claim 1, wherein the part connected with the movement mechanism meant for the X-ray detector unit is adapted to be turned aside for the duration of cephalostatic imaging so that the X-ray beam emitted by the X-ray source will propagate substantially unobstructed to an X-ray detector placed on another means of support to take a cephalostatic image.

16. A movement mechanism according to claim 1, wherein the part connected with the movement mechanism meant for the X-ray source is adapted to be turned aside for the duration of cephalostatic imaging so that the X-ray beam emitted by the X-ray source placed on another means of support will propagate substantially unobstructed to an X-ray detector to take a cephalostatic image.

17. A movement mechanism according to claim 1, wherein said parts of the movement mechanism are at an angle with respect to each other during the imaging session.

18. An extraoral dental X-ray apparatus comprising a movement mechanism according to claim 1.

* * * * *